Sept. 11, 1956 F. W. ANDERSON Plant Pat. 1,516

PEACH TREE

Filed Nov. 7, 1955

WITNESS

Addison E. Avery

INVENTOR

Frederic W. Anderson

Webster & Webster

ATTYS.

United States Patent Office

Plant Pat. 1,516
Patented Sept. 11, 1956

1,516

PEACH TREE

Frederic W. Anderson, Merced, Calif.

Application November 7, 1955, Serial No. 545,587

1 Claim. (Cl. 47—62)

This invention relates to a new and distinct variety of peach tree characterized by the bearing of large, firm, highly colored, yellow fleshed fruit which is especially desirable for commercial production; the primary feature of novelty being that the variety has a ripening period earlier than any other yellow fleshed variety of peach of which I have knowledge.

This early ripening characteristic of the fruit of the present variety of peach tree brings it into harvest about a week before the yellow fleshed Blazing Gold peach (United States Plant Patent No. 1,127) and only about three days later than the white fleshed Mayflower peach (unpatented).

By additional comparison, the fruit of the present variety of peach is somewhat larger in size and more attractive in appearance than the Blazing Gold peach; and larger, more productive, firmer, and generally better market quality than the Mayflower peach.

The fruit of the instant variety is more specifically characterized, as to color, by a yellow ground color almost completely over-spread with an attractive bright red color at maturity; and—as to pubescence—by the same being very short and inconspicuous, as is desirable for a market peach.

The present variety of peach tree was originated by me in my experimental orchard at Le Grand, California, under conditions of close inspection and continuing comparison with other varieties, in the following manner:

Flowers of a Le Grand nectarine (United States Plant Patent No. 974) were fertilized with pollen from a group of seedlings of the July Elberta peach (United States Plant Patent No. 15), which produced early ripening peaches. Seeds from the latter were planted, and the resulting seedlings were all peach trees which bore yellow fleshed fruit. Open-pollinated flowers of these latter peach trees produced seeds which I gathered and planted, and of which the resulting seedlings were approximately one-fourth nectarines and three-fourths peaches; one of the latter having evidenced an extremely early ripening period, and is the present variety.

After I recognized its distinctive features and commercial potential—and selected it—asexual reproduction was accomplished by me in my experimental orchard as aforesaid, by top working—specifically by budding—on mature orchard trees. Such asexual reproductions were found to carry forward all of the characteristics of the parent.

Figure 1:
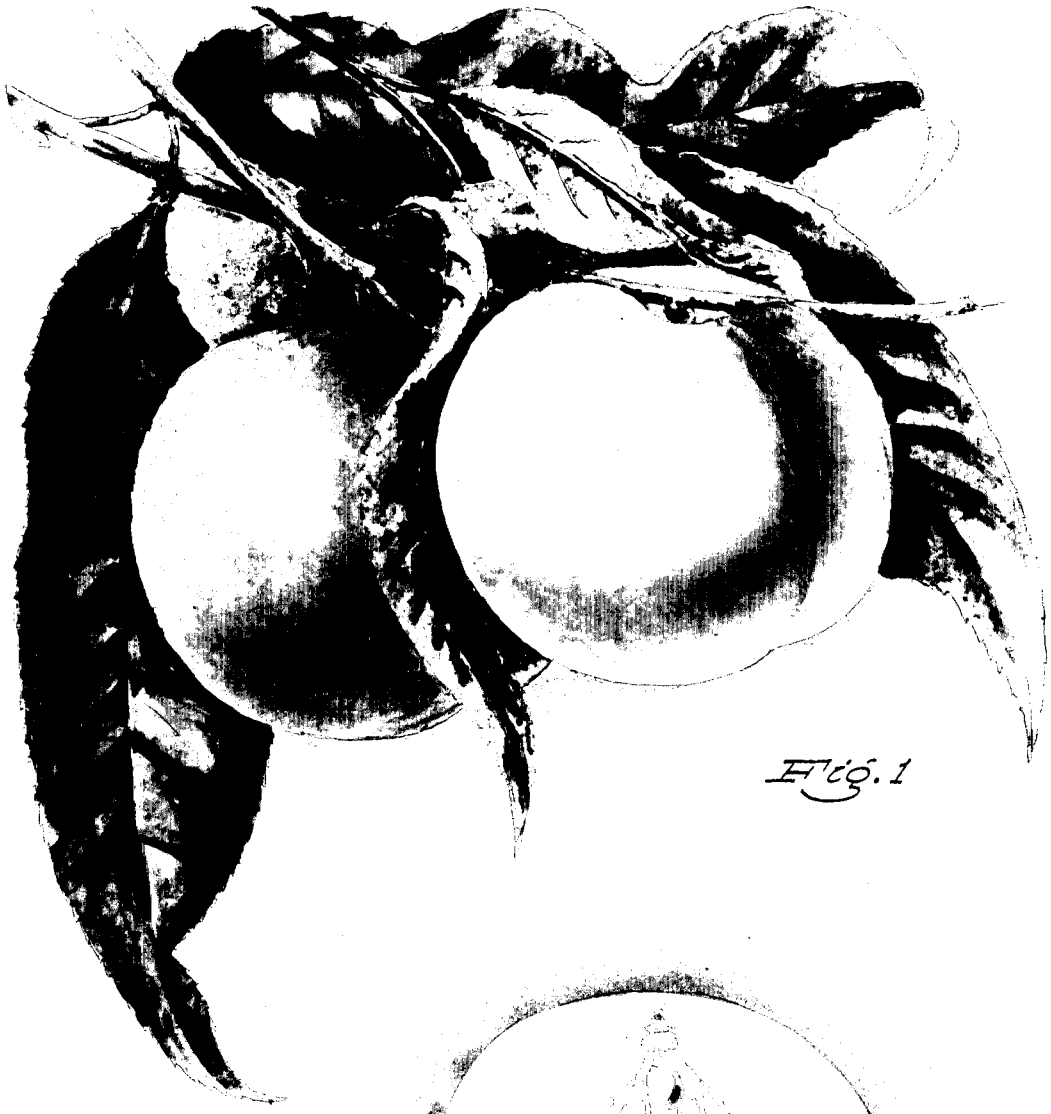
Fig. 1 is an elevation showing two of the fruit, together with twigs and leaves.
Figure 2:
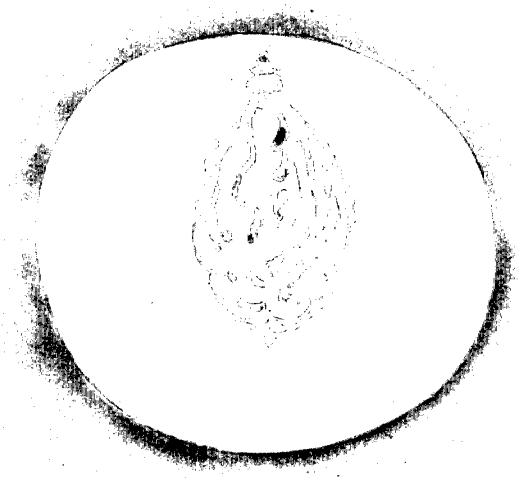
Fig. 2 is a sectional elevation of one of the fruit, with the stone exposed.

Referring now more specifically to the pomological details of this new and distinct variety of peach tree, the following is an outline description thereof; all major color plate identifications being by reference to Maerz and Paul Dictionary of Color:

Tree:
- *Size.*—Large to medium.
- *Vigor.*—Vigorous.
- *Growth.*—Upright to spreading.
- *Density.*—Open.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Lenticels.*—Medium number; medium size.

Leaves:
- *Size.*—Medium. Average length—6½". Average width—1⅜".
- *Thickness.*—Medium.
- *Margin.*—Crenate.
- *Petiole.*—Medium length; medium thickness.
- *Glands.*—Average number—three. Reniform. Usually positioned two on petiole and one or more on blade.
- *Stipules.*—None.
- *Color.*—Top side—medium green (22–L–8). Under side—lighter green (21–K–7).

Flower buds:
- *Size.*—Medium.
- *Form.*—Conic.

Flowers:
- *Blooming period.*—First and full bloom about with the July Elberta peach. Early to medium blooming period as compared with other varieties.
- *Size.*—Medium.

Fruit:
- *Maturity when described.*—Hard ripe.
- *Date of first picking.*—June 10, 1955.
- *Date of last picking.*—June 19, 1955.
- *Size.*—Uniform. Large to medium. Average diameter axially—2½". Average transversely in suture plane—2½".
- *Form.*—Uniform; symmetrical; globose.
- *Suture.*—Shallow, extends from base to pistil point, with slight depression beyond.
- *Ventral surface.*—Rounded; strongly lipped; lips equal.
- *Cavity.*—Rounded. Elongated in suture plane, with suture showing on one side. Average depth—⅜". Average breadth—½".
- *Base.*—Oblique.
- *Apex.*—Short.
- *Pistil point.*—Apical.

Skin:
- *Thickness.*—Medium.
- *Texture.*—Tough to medium; tenacious to flesh.
- *Tendency to crack.*—None in wet seasons.
- *Down.*—Short.
- *Color.*—Under-color—yellow (9–L–6). Over-color—almost completely overspread, at maturity, with a bright red (6–L–6), with some variance depending on exposure to sunlight.

Flesh:
- *Juice.*—Moderate.
- *Texture.*—Firm; meaty.
- *Fibers.*—Few.
- *Ripens.*—Even.
- *Flavor.*—Sub-acid.
- *Aroma.*—Wanting.
- *Eating quality.*—Good.
- *Color.*—Light yellow (9–J–4) shading to darker yellow (10–J–5) adjacent the stone, and also shading darker yellow (9–K–6) toward the skin.

Stone:

*Type.*—Semi-free to cling; i. e. genetically free, but phenotypically cling.
*Size.*—Medium. Average length—1⅛". Average breadth—1 1/16". Average thickness—¾".
*Form.*—Oblong.
*Base.*—Oblique.
*Hilum.*—Oblong.
*Apex.*—Rounded.
*Sides.*—Equal.
*Ridges.*—Rounded.
*Pits.*—Elongated.
*Ventral edge.*—Thick.
*Dorsal edge.*—Full, with shallow groove.
*Color.*—Light tan (10–D–5 to 10–F–7).

Use: Market.

Shipping quality: Good.

The tree and its fruit herein described may vary in slight detail due to climatic and soil conditions under which the variety may be grown.

The following is claimed:

A new and distinct variety of peach tree, as illustrated and described, characterized by large sized, firm, yellow fleshed, highly colored, semi-free to clingstone fruit having a ripening period approximately one week earlier than the Blazing Gold peach and approximately three days later than the Mayflower peach; and—by further comparison—being larger and more attractive than the Blazing Gold peach, and being larger, yellow instead of white fleshed, firmer, and more productive than the Mayflower peach; and additionally characterized by fruit which has very short and inconspicuous pubescence, and a skin color which is a light yellow almost completely over-spread with a bright red color at maturity.

No references cited.